United States Patent
Kim (10) Patent No.: US 9,631,976 B2
(45) Date of Patent: Apr. 25, 2017

(54) MINIATURE SPECTROMETER AND APPARATUS EMPLOYING SAME

(71) Applicant: SAMSUNG ELECTRONICS CO., LTD., Suwon-si (KR)

(72) Inventor: Dongho Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 80 days.

(21) Appl. No.: 14/684,624

(22) Filed: Apr. 13, 2015

(65) Prior Publication Data

US 2016/0061660 A1  Mar. 3, 2016

(30) Foreign Application Priority Data

Aug. 26, 2014 (KR) .................. 10-2014-0111630

(51) Int. Cl.
*G01J 3/30* (2006.01)
*G01J 3/02* (2006.01)
*A61B 5/1455* (2006.01)
*A61B 5/145* (2006.01)
*G01J 3/44* (2006.01)

(52) U.S. Cl.
CPC .......... *G01J 3/0205* (2013.01); *A61B 5/1455* (2013.01); *A61B 5/14532* (2013.01); *G01J 3/0259* (2013.01); *G01J 3/44* (2013.01); *A61B 2562/028* (2013.01)

(58) Field of Classification Search
CPC . G01J 3/44; G01J 3/0205; G01J 3/108; A61B 5/1455; A61B 5/14532
See application file for complete search history.

(56) References Cited

U.S. PATENT DOCUMENTS

| 2010/0182598 A1* | 7/2010 | Choi ................. G01J 3/02 356/323 |
| 2011/0116735 A1* | 5/2011 | Baets ................ G01D 5/268 385/12 |
| 2012/0243821 A1 | 9/2012 | Belkin et al. |

(Continued)

FOREIGN PATENT DOCUMENTS

| JP | 4921213 B2 | 4/2012 |
| KR | 10-0865755 B1 | 10/2008 |
| KR | 10-1249240 B1 | 4/2013 |

OTHER PUBLICATIONS

Koichi Okamoto et al; "Surface-plasmon-enhanced light emitters based on InGaN quantum wells"; Nature Materials; vol. 3; Sep. 2004; pp. 601-605.

(Continued)

*Primary Examiner* — Abdullahi Nur
(74) *Attorney, Agent, or Firm* — Sughrue Mion, PLLC (57) ABSTRACT

A miniature spectrometer and a miniature spectrometer module employing the same are disclosed. The disclosed miniature spectrometer includes: a band-pass filter which is configured to transmit input light in a surface plasmon mode and which has an array of waveguides which are configured to output a plurality of different transmission wavelength bands; an in-coupler configured to couple the transmitted input light to a first end of the array of waveguides; and an array of optical detectors configured to detect respective lights which are output from a second end of the array of waveguides.

19 Claims, 5 Drawing Sheets

(56) References Cited

U.S. PATENT DOCUMENTS

2012/0250720 A1  10/2012  Deleon et al.
2014/0114151 A1* 4/2014  Miller .................. A61B 5/1455
                                                      600/322

OTHER PUBLICATIONS

Jongwon Lee et al; "Broadly wavelength tunable bandpass filters based on long-range surface plasmon polaritons"; Optic Letters; vol. 36; No. 19; Oct. 1, 2011; pp. 3744-3746.

* cited by examiner

MINIATURE SPECTROMETER AND APPARATUS EMPLOYING SAME

CROSS-REFERENCE TO RELATED APPLICATION

This application claims priority from Korean Patent Application No. 10-2014-0111630, filed on Aug. 26, 2014, in the Korean Intellectual Property Office, the disclosure of which is incorporated herein by reference in its entirety.

BACKGROUND

1. Field

Exemplary embodiments relate to a spectrometer and an apparatus employing the same, and more particularly, to a miniature spectrometer and an apparatus employing the same.

2. Description of the Related Art

A method being currently discussed with a relatively high possibility as a method of noninvasively measuring a blood sugar level is a method using optics. Two particularly feasible methods among methods of noninvasively measuring a blood sugar level by using optics are a near-infrared (NIR) absorption spectral analysis method and a laser Raman spectroscopy method. The NIR absorption spectral analysis method is a method of analyzing light which is emitted out of the skin through diffused reflection after irradiating broadband NIR rays on the skin in order to calculate the intensity of light absorbed by blood sugar molecules in the skin and to predict a blood sugar level. The laser Raman spectroscopy method is a method of analyzing a blood sugar level by obtaining a Raman shift via an analysis on wavelengths of light emitted from the skin after irradiating a laser beam on the skin. In these two methods, a bulky grating is mandatory to analyze a spectrum of light.

As such, a grating is necessary for a spectrometer for splitting light, and a considerable space for the lights split by the grating to approach an optical detector is necessary to secure resolution. Due to such a volume characteristic of the spectrometer, there are many restrictions in the manufacture of a wrist-oriented noninvasive blood sugar sensor.

SUMMARY

Provided are a miniature spectrometer which is realizable in a chip shape and an apparatus employing the same.

Additional aspects will be set forth in part in the description which follows and, in part, will be apparent from the description, or may be learned by practice of the presented exemplary embodiments.

According to an aspect, a miniature spectrometer includes: a band-pass filter which is configured to transmit input light in a surface plasmon mode and which has an array of waveguides configured to output a plurality of different transmission wavelength bands; an in-coupler configured to couple the transmitted input light to a first end of the array of waveguides; and an array of optical detectors configured to detect respective lights output from a second end of the array of waveguides.

The band-pass filter may include: a base layer formed of a first dielectric material; a plurality of metal stripes formed on the base layer; and an array of cover layers configured to respectively cover the plurality of metal stripes with a second dielectric material that is different from the first dielectric material, wherein each respective waveguide in the array of waveguides is formed by the base layer, a corresponding metal stripe, and a corresponding cover layer.

Each respective cover layer included in the array of cover layers may be formed with a different respective refractive index which corresponds to a respective transmission wavelength band.

The cover layers included in the array of cover layers may be spaced apart from each other.

Each of the plurality of metal stripes may be buried in the base layer such that an upper surface thereof is exposed.

Each of the plurality of metal stripes may be formed such that at least a portion thereof protrudes from the base layer.

Each of the plurality of metal stripes may have a respective width which is less than or equal to about 10 μm.

Each of the plurality of metal stripes may have a respective thickness which is less than or equal to about 100 nm.

The in-coupler may be disposed so as to direct the input light to at least one of a boundary surface between a respective metal stripe and a respective cover layer and a boundary surface between a respective metal stripe and the base layer for each of the array of waveguides.

The in-coupler may include a grating in-coupler.

The grating in-coupler may have a period which is less than or equal to about 10 μm.

The array of optical detectors may be integrated with the second end of the array of waveguides.

According to another aspect, a miniature spectrometer module includes: a light source configured to irradiate excited light upon an object; and a miniature spectrometer configured to sense scattered light which is generated due to the irradiation of the excited light upon the object.

The miniature spectrometer module may further include a base, wherein the light source is disposed on a first surface of the base and the miniature spectrometer is disposed on at least one of the first surface of the base and a second surface of the base which is different from the first surface.

The base may be formed of a flexible material.

The miniature spectrometer module may be configured to be wearable on the object.

The miniature spectrometer may be configured to sense at least one of scattered light reflected from the object and scattered light which has propagated through the object.

The miniature spectrometer module may further include a signal processor configured to analyze at least one physical property of the object based on a signal sensed by the miniature spectrometer.

The miniature spectrometer module may further include a display configured to display a result analyzed by the signal processor.

The miniature spectrometer module may be configured to analyze at least one physical property of the object based on at least one of a near-infrared (NIR) absorption spectral analysis method which includes irradiating light of an NIR band from the light source and a laser Raman spectroscopy method which includes irradiating a laser beam from the light source.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Hereinafter, a miniature spectrometer and an apparatus employing the same, according to exemplary embodiments, will be described in detail with reference to the accompanying drawings, wherein like reference numerals refer to like elements throughout, and in the drawings, the thicknesses or sizes of components may be exaggerated for convenience and clarity of description. In addition, the exemplary embodiments described below are only illustrative, and various modifications may be performed from these exemplary embodiments. In addition, in the layer structure described below, the expression of "above" or "on" may include both the expression of contacting and directly on and the expression of on without contacting.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present disclosure.

When a thin metal layer is in contact with a dielectric material, if an electromagnetic wave having specific energy is irradiated, a surface plasmon mode is formed on the surface of the metal. Based on this, long range surface plasmon polaritons (LRSPP) may be produced in a structure in which a thin metal is inserted between two dielectric materials. In this case, when a metal stripe is formed between two dielectric materials having different index dispersions, light of a specific wavelength band may be transmitted.

Figure 1:
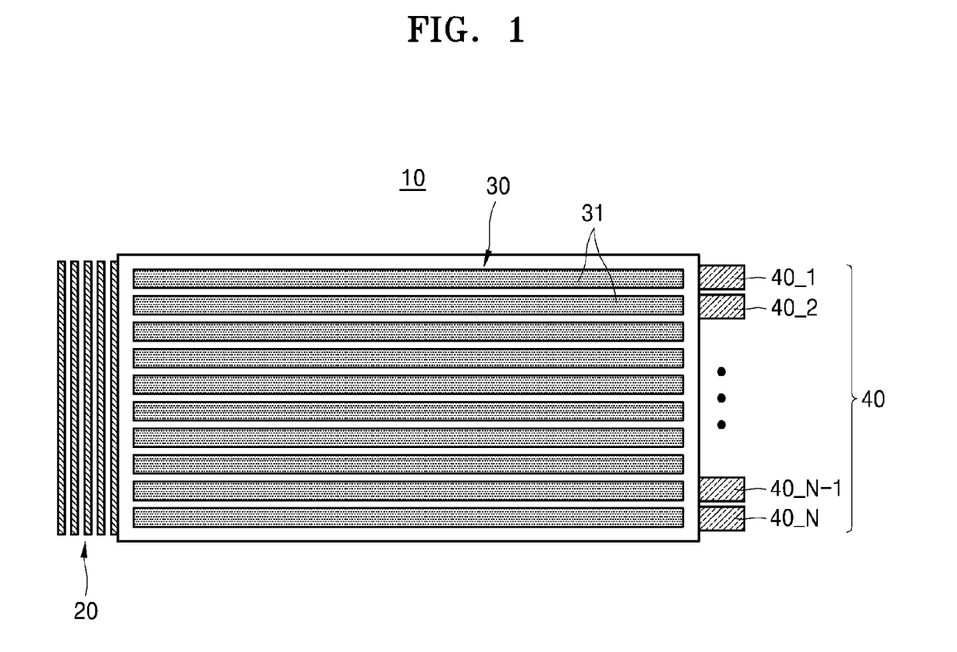
FIG. 1 illustrates a miniature spectrometer, according to an exemplary embodiment.

FIG. 1 illustrates a miniature spectrometer 10, according to an exemplary embodiment.

Referring to FIG. 1, the miniature spectrometer 10 includes a band-pass filter unit (also referred to herein as a "band pass filter") 30 configured for transmitting input light in a surface plasmon mode, an in-coupler 20, and an array of optical detectors 40.

The band-pass filter unit 30 may include an array of waveguides 31 which are configured to output a plurality of different transmission wavelength bands, wherein each waveguide 31 in the array of waveguides 31 is formed in a stack structure of a metal and a dielectric so as to form a surface plasmon mode on a surface of the metal in response to input light and to transmit the surface plasmon mode. For example, each waveguide 31 in the array of waveguides 31 of the band-pass filter unit 30 may be formed so as to form long range surface plasmon polaritons (LRSPP) in a structure in which a thin metal is inserted between two dielectric materials. In this case when a metal stripe is formed between two dielectric materials having different index dispersions, light of a specific wavelength band may be transmitted.

Figure 2:
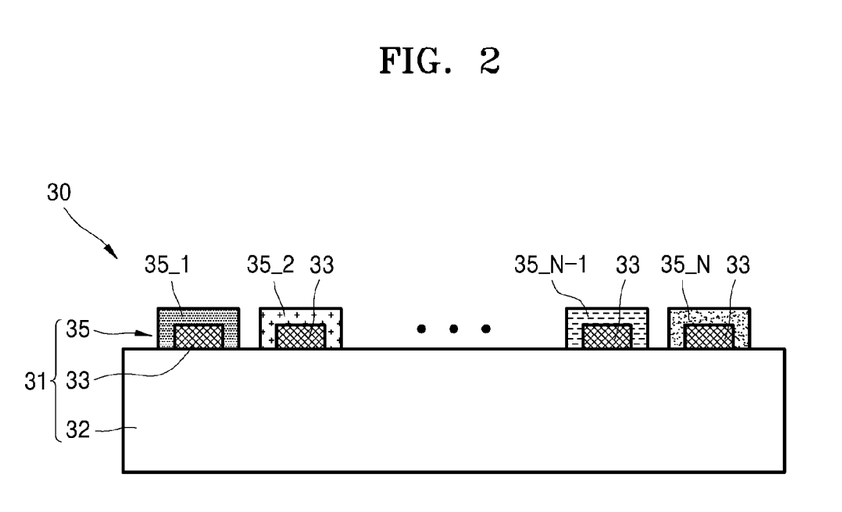
FIGS. 2 and 3 illustrate examples of a band-pass filter unit in the miniature spectrometer of FIG. 1, according to one or more exemplary embodiments.
Figure 3:
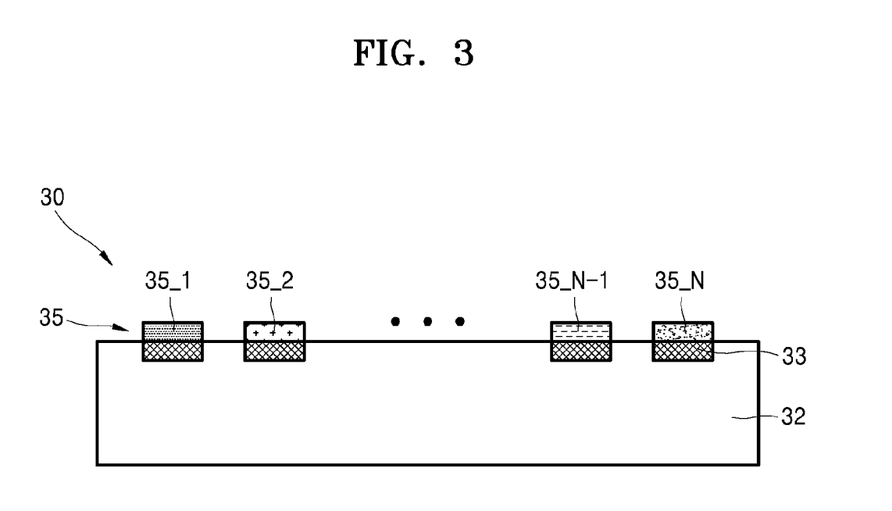

Referring to FIGS. 2 and 3, the band-pass filter unit 30 may include a base layer 32, a plurality of metal stripes 33 formed on the base layer 32 and spaced apart from each other, and an array of cover layers 35 provided so as to respectively cover the metal stripes 33. Herein, each of the base layer 32 and the array of cover layers 35 may be formed of a dielectric material.

The metal stripes 33 may be formed such that at least a portion thereof protrudes from the base layer 32, as shown in FIG. 2, or formed to be buried in the base layer 32, except for upper surfaces thereof, which are thereby exposed, as shown in FIG. 3. FIG. 2 illustrates an example in which the whole metal stripes 33 protrude from the base layer 32. Herein, the metal stripes 33 may be spaced apart from each other, and first to Nth cover layers 35_1, 35_2, ..., 35_N-1, and 35_N in the array of cover layers 35 may be formed spaced apart from each other such that the array of cover layers 35 respectively correspond to the separate metal stripes 33.

Each of the metal stripes 33 may have a width of, for example, about 10 μm or less. In addition, a thickness of each of the metal stripes 33 may be formed to be, for example, about 100 nm or less.

As described above, when the metal stripes 33 are formed on the base layer 32, and the array of cover layers 35 is formed such that the cover layers 35 respectively cover the metal stripes 33, each of the separate waveguides 31 in the array of waveguides 31 is formed by the base layer 32, its corresponding metal stripe 33, and its corresponding cover layer 35_1, 35_2, ..., 35_N-1, or 35_N. In this case, the waveguides 31 may be formed in parallel to each other in an integrated structure.

The base layer 32 may be formed of a first dielectric material, and the array of cover layers 35 may be formed of a second dielectric material that is different from the first dielectric material. Herein, the first to Nth cover layers 35_1, 35_2, ..., 35_N-1, and 35_N in the array of cover layers 35 may be formed of different second dielectric materials so as to cause transmission wavelength bands of the array of cover layers 35 to be different from each other. In particular, when the array of cover layers 35 includes the first to Nth cover layers 35_1, 35_2, ..., 35_N-1, and 35_N, the first to Nth cover layers 35_1, 35_2, ..., 35_N-1, and 35_N may be formed so as to respectively have refractive indexes of $n_1, n_2, \ldots, n_N$ (wherein, $n_1 \neq n_2 \neq \ldots \neq n_N$).

As such, when N metal stripes 33 are provided as an array, the first to Nth cover layers 35_1, 35_2, ..., 35_N-1, and 35_N are formed so as to respectively cover the N metal stripes 33, if the first to Nth cover layers 35_1, 35_2, ..., 35_N-1, and 35_N are formed of second dielectric materials of which refractive indexes are slightly different from each other, each of the second dielectric materials of the first to Nth cover layers 35_1, 35_2, ..., 35_N-1, and 35_N has an index dispersion with respect to a wavelength, and thus, index dispersion matching between a second dielectric material of each of the first to Nth cover layers 35_1, 35_2, ..., 35_N-1, and 35_N and the first dielectric material of the base layer 32 is achieved at different wavelengths. Accordingly, for the first to Nth cover layers 35_1, 35_2, ..., 35_N-1, and 35_N, only light of a wavelength at which index dispersion matching is possible with a refractive index of the base layer 32 is separated (split) and guided through the corresponding metal strips 33.

Therefore, according to the band-pass filter 30 described above, incident light may be split according to wavelengths by forming the array of cover layers 35 so as to respectively cover the metal stripes 33 such that refractive indexes of the cover layers 35 are slightly different from each other.

Instead of forming the array of cover layers 35 of different second dielectric materials, portions of the base layer 32, which respectively correspond to the waveguides 31, may be formed of different first dielectric materials, and the array of cover layers 35 may be formed of a same second dielectric material. Even in this case, incident light may be split according to wavelengths by forming the portions of the base layer 32, which respectively correspond to the waveguides 31, so that refractive indexes of their corresponding portions are slightly different from each other.

The in-coupler 20 couples light to a first end of the array of waveguides 31. The in-coupler 20 may include, for example, a grating in-coupler. In this case, the grating in-coupler may be formed so that a period thereof is about 10 μm or less, e.g., about 1 μm or less.

The in-coupler 20 may be disposed so that light is incident to a boundary surface between a dielectric material of each waveguide 31 and a metal, which jointly form the band-pass filter unit 30. In particular, the in-coupler 20 may be disposed so that light is incident to a boundary surface between a respective metal stripe 33 and its corresponding cover layer 35 of each waveguide 31, or to a boundary surface between the respective metal stripe 33 and the base layer 32 of each waveguide 31.

When the grating in-coupler is provided as described above, the in-coupler 20 may be integrated with the array of waveguides 31.

The array of optical detectors 40 is provided to detect respective lights which output from a second end (which is opposite the first end) of the array of waveguides 31, is located at the end portion of each waveguide 31, and detects respective lights which are split for each wavelength by the band-pass filter unit 30. Each of first to Nth optical detectors 40_1, 40_2, . . . , 40_N−1, and 40_N in the array of optical detectors 40 may be integrated with the end portion of each respective waveguide 31 in the array of waveguides 31.

When the in-coupler 20 using a grating and the band-pass characteristic of the LRSPP are used, the miniature spectrometer 10 may be a chip-type miniature spectrometer. In this case, the in-coupler 20 functions to couple light emitted from the skin to a chip functioning as a spectrometer when, for example, light is irradiated by a light source, such as a laser device (LD) or a light-emitting device (LED), for noninvasive blood sugar measurement.

Therefore, the in-coupler 20, the band-pass filter unit 30, and the array of optical detectors 40 may be implemented as an on-chip. In particular, the miniature spectrometer 10 according to the present exemplary embodiment may be implemented as a miniature on-chip spectrometer.

According to the miniature spectrometer 10 according to the present exemplary embodiment, for example, signals of lights which are split for each wavelength may be detected by irradiating light emitted by a light source toward the skin, condensing light of a wide spectrum, which is emitted from the skin, by using the in-coupler 20, splitting the condensed light via the array of waveguides 31 of the band-pass filter unit 30, and detecting the split lights by using the first to Nth optical detectors 40_1, 40_2, . . . , 40_N−1, and 40_N located at the end portions of the waveguides 31.

The principle of splitting light by causing the refractive indexes of the second dielectric materials of the first to Nth cover layers 35_1, 35_2, . . . , 35_N−1, and 35_N in the array of cover layers 35 to be slightly different from each other is as described below.

Figure 4:
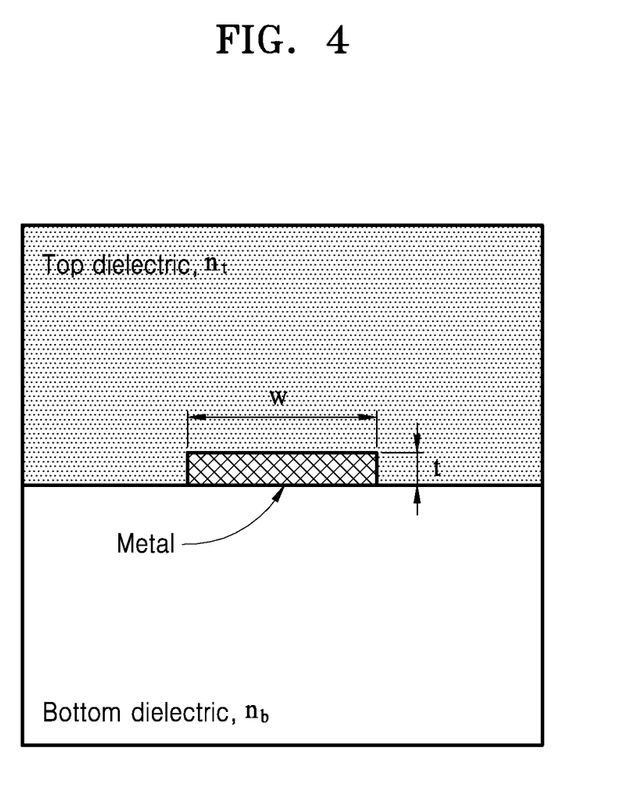
FIG. 4 illustrates a structure in which a top dielectric having a refractive index $n_t$ covers a metal layer on a bottom dielectric having a refractive index $n_b$.

FIG. 4 illustrates a structure in which a top dielectric having a refractive index $n_t$ covers a metal layer on a bottom dielectric having a refractive index $n_b$. FIG. 4 illustrates a case in which the metal layer is formed of gold (Au) and has a width of about 4 μm and a thickness of about 20 nm, and a near-infrared (NIR) light of which λ=1.55 μm is incident to the structure.

For example, in the structure of FIG. 4, a case in which the respective refractive indexes of the top dielectric and the bottom dielectric are the same ($n_b=n_t=1.50$) and a case in which the respective refractive indexes of the top dielectric and the bottom dielectric are slightly different from each other ($n_b=1.50$, and $n_t=1.5014$) are considered.

When index dispersion matching is achieved since the refractive indexes of the top dielectric and the bottom dielectric are the same (symmetric cladding), a mode is well confined, and thus, transmission loss is very low.

However, when index dispersion mismatch occurs due to a slight difference between the respective refractive indexes of the top dielectric and the bottom dielectric (asymmetric cladding), a mode is distorted, and a leakage mode is generated.

Therefore, for lossless transmission of a mode, it is recommended that index dispersion matching of the top dielectric and the bottom dielectric surrounding the metal layer be implemented.

A dielectric material has an effective refractive index which varies according to a wavelength, because an index dispersion according a wavelength exists.

For example, because wavelength regions at which index dispersion matching is achieved between an $SiO_2$ material and a plurality of types of materials having slightly different respective refractive indexes are different from each other, transmission peak wavelengths are different from each other.

Therefore, as in the miniature spectrometer 10 according to the exemplary embodiment described above, when the array of waveguides 31 is formed by forming the metal stripes 33 on the base layer 32 formed of the first dielectric material and forming the first to Nth cover layers 35_1, 35_2, . . . , 35_N−1, and 35_N in the array of cover layers 35 formed of the second dielectric materials, which respectively cover the metal stripes 33, so that the first to Nth cover layers 35_1, 35_2, . . . , 35_N−1, and 35_N have slightly different respective refractive indexes, wavelength regions at which index dispersion matching is achieved in the waveguides 31 are different from each other, and accordingly, incident light may be split according to wavelengths.

Because the miniature spectrometer 10 according to the exemplary embodiment described above may be miniaturized enough to be implemented as an on-chip, whereas a conventional spectrometer has a relatively large volume due to the use of a grating for splitting light by using a diffraction angle difference according to wavelengths of the light, the miniature spectrometer 10 may be comparatively easily applied to a wrist-oriented noninvasive sensor and the like.

Figure 5:
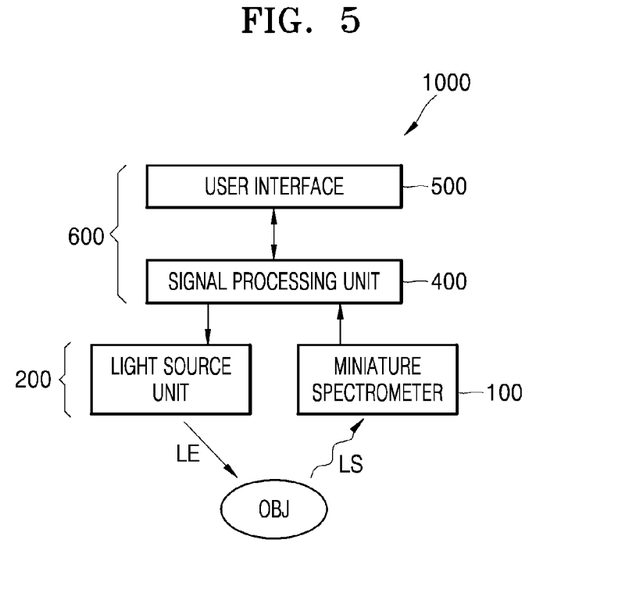
FIG. 5 is a block diagram of a miniature spectrometer module, according to an exemplary embodiment.

FIG. 5 illustrates a block diagram of a miniature spectrometer module 1000, according to an exemplary embodiment.

The miniature spectrometer module 1000 includes a light source unit (also referred to herein as a "light source device") 300 configured for irradiating excited light LE upon an object OBJ and a miniature spectrometer 100 configured for sensing scattered light LS received from the object OBJ.

The object OBJ may include any of a human body, an organism of an animal or the like, food, and/or the like. For example, the object OBJ may be any of a human body for which a blood sugar level is measured, food for which freshness is measured, or one of other samples to be used to analyze air pollution, water pollution, and the like.

The light source unit 200 may include a light source and further include at least one optical element configured for controlling light emitted from the light source to be oriented with respect to a desired position of the object OBJ. The light source may be configured so as to irradiate light of a wavelength band that is suitable for a nature of the object OBJ to be analyzed. For example, the light source may irradiate light of an NIR band, e.g., an NIR light of a wavelength band having wavelengths which fall within a range of about 0.8 µm to about 2.5 µm. For the light source, an LED and/or a laser light source may be provided.

For the miniature spectrometer 100, the miniature spectrometer 10 described with reference to FIGS. 1, 2, and 3 may be applied.

The miniature spectrometer module 1000 may further include a control unit (also referred to herein as a "controller") 600 configured for analyzing the physical properties of the object OBJ based on a signal sensed by the miniature spectrometer 100 and for generating a corresponding control signal. The control unit 600 may include a user interface 500 and a signal processing unit (also referred to herein as a "signal processor") 400. The user interface 500 may include an input unit (also referred to herein as an "input device") (not shown) and a display unit (also referred to herein as a "display device" and/or as a "display") (not shown). The signal processing unit 400 may analyze the physical properties of the object OBJ based on a signal sensed by the miniature spectrometer 100, for example, by implementing at least one of an NIR absorption spectral analysis method or a Raman spectroscopy method.

The NIR absorption spectral analysis method is a method for analyzing light emitted out of the object OBJ via diffused reflection after broadband NIR rays have been irradiated upon the object OBJ in order to calculate the intensity of light absorbed by, for example, blood sugar molecules contained in the object OBJ and to predict a blood sugar level. The Raman spectroscopy method is a method for analyzing, for example, a blood sugar level by obtaining a Raman shift via an analysis on wavelengths of light emitted from the object OBJ after a laser beam has been irradiated upon the object OBJ. The Raman spectroscopy method uses scattering, specifically inelastic scattering, such that light incident into the object OBJ collides with atoms and/or molecules contained in the object OBJ and is thusly scattered in various directions. The scattering does not indicate simple reflection from the surfaces of atoms and/or molecules, but indicates emission after being absorbed into atoms and/or molecules, and thus scattered light has a wavelength that is longer than that of incident light. This wavelength difference may be less than or equal to about 200 nm. By analyzing a spectrum of the scattered light, any of various physical properties of the object OBJ, such as vibration of a molecule, a structure of the molecule, and the like, may be analyzed.

The signal processing unit 400 may process the analyzed result as an image signal so as to display the analyzed result on the display unit of the user interface 500. In addition, the signal processing unit 400 may transmit a control signal to the light source unit 200 in response to an input received from the user interface 500. The signal processing unit 400 may be implemented by a microprocessor and/or the like.

The miniature spectrometer 100 and the control unit 600 may be connected to each other in a wired or wireless manner. For example, the miniature spectrometer module 1000 may be implemented by a small-sized portable device in which the miniature spectrometer 100 and the control unit 600 are connected in a wired manner. Alternatively, the control unit 600 may be included in a portable mobile communication device and may communicate with the miniature spectrometer 100 in a wireless manner.

Figure 6:
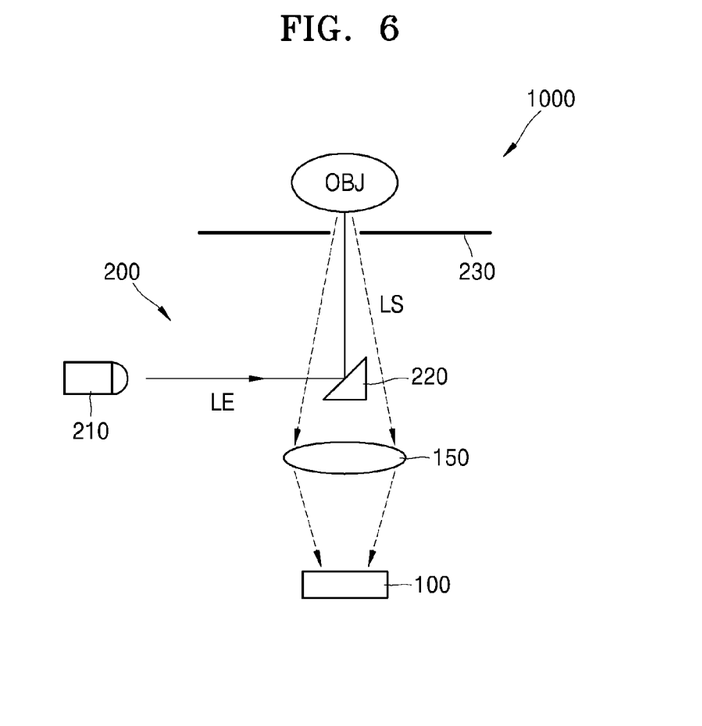
FIG. 6 illustrates an optical arrangement of the miniature spectrometer module of FIG. 5, according to an exemplary embodiment.

FIG. 6 illustrates an optical arrangement of the miniature spectrometer module 1000 of FIG. 5, according to an exemplary embodiment.

Referring to FIG. 6, the miniature spectrometer module 1000 is of a reflective type and may include an optical system which is configured so that the miniature spectrometer 100 senses scattered light LS reflected from the object OBJ.

The light source unit 200 may include a light source 210, an optical path changer 220, an iris 230, and the like. Although the optical path changer 220 is shown in a prism form, this is only illustrative, and the optical path changer 220 may have an alternative form, such as, for example, a form of a beam splitter or a flat mirror. The optical path changer 220 may be omitted according to a disposed position of the light source 210.

The miniature spectrometer module 1000 may further include an optical lens 150 configured for condensing the scattered light LS from the object OBJ and directing the condensed scattered light into the miniature spectrometer 100.

The excited light LE irradiated by the light source 210 collides with a molecular structure contained in the object OBJ, is absorbed by the molecular structure, and re-emitted from the object OBJ in a form of wavelength-changed scattered light LS. The scattered light LS, i.e., an organism optical signal, includes various spectra of which a wavelength-changed grade varies according to a corresponding molecular state inside the object OBJ. The miniature spectrometer module 1000 according to the present exemplary embodiment employs an optical system structure in which the scattered light LS which propagates along the same path as that along which the excited light LE is incident to the object OBJ is incident to the miniature spectrometer 100, and according to circumstances, an additional optical device configured for dividing and redirecting the scattered light LS towards the miniature spectrometer 100 may be further employed.

Figure 7:
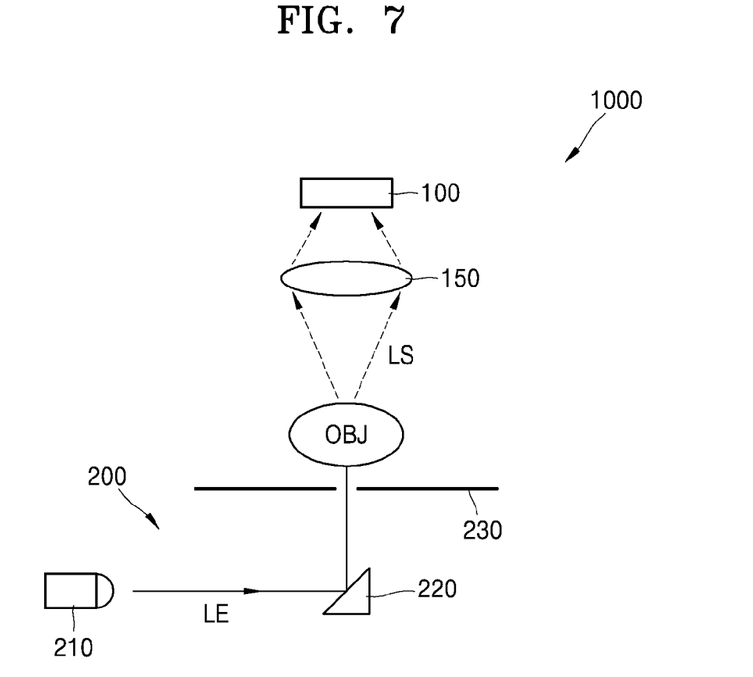
FIG. 7 illustrates an optical arrangement of the miniature spectrometer module of FIG. 5, according to another exemplary embodiment.

FIG. 7 is an optical arrangement of the miniature spectrometer module 1000 of FIG. 5, according to another exemplary embodiment.

Referring to FIG. 7, the miniature spectrometer module 1000 is of a transmissive type and may include an optical system which is configured so that the miniature spectrometer 100 senses scattered light LS, which has propagated through the object OBJ.

The light source unit 200 may include the light source 210, the optical path changer 220, the iris 230, and the like. Although the optical path changer 220 is shown in a prism form, this is only illustrative, and the optical path changer 220 may have an alternative form, such as, for example, a form of a beam splitter or a flat mirror. The optical path changer 220 may be omitted according to a disposed position of the light source 210.

The miniature spectrometer module 1000 may further include the optical lens 150 which is configured for condensing the scattered light LS received from the object OBJ and directing the condensed scattered light into the miniature spectrometer 100.

The excited light LE irradiated by the light source 210 collides with a molecular structure contained in the object OBJ, is absorbed by the molecular structure, and re-emitted from the object OBJ in a form of wavelength-changed scattered light LS. The scattered light LS, i.e., an organism optical signal, includes various spectra of which a wavelength-changed grade varies according to a corresponding molecular state inside the object OBJ. The miniature spectrometer module 1000 according to the present exemplary embodiment employs an optical system structure in which the scattered light LS, which has propagated through the object OBJ, is incident to the miniature spectrometer 100.

The reflective type of spectrometer, as shown in FIG. 6, or the transmissive type of spectrometer, as shown in FIG. 7, is selected based on the nature of the object OBJ.

Figure 8:
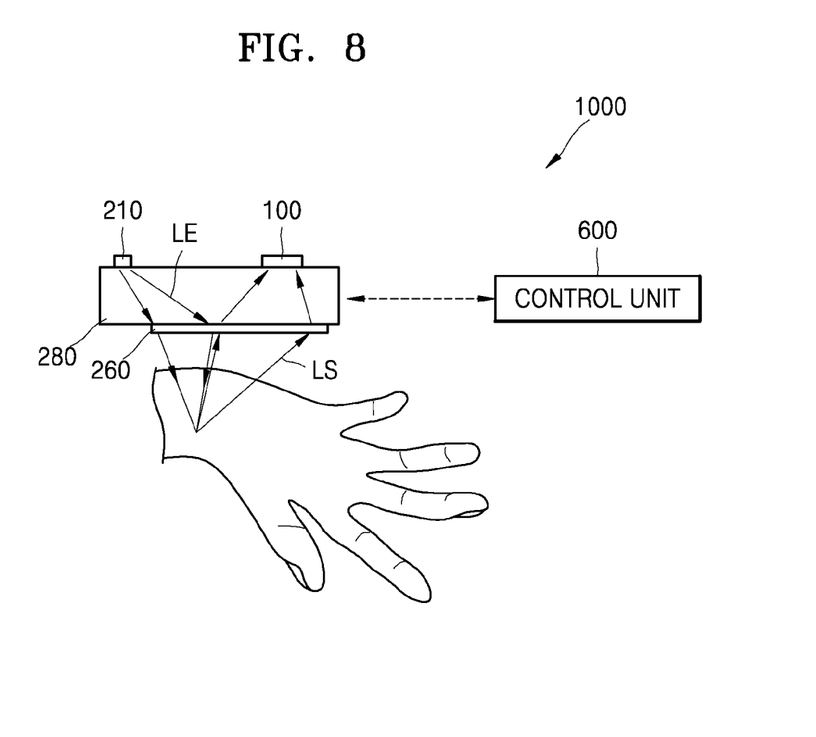
FIG. 8 illustrates an optical arrangement of the miniature spectrometer module of FIG. 5, according to another exemplary embodiment.

FIG. 8 illustrates an optical arrangement of the miniature spectrometer module 1000 of FIG. 5, according to another exemplary embodiment.

Referring to FIG. 8, the miniature spectrometer module 1000 further includes a base 280, and the light source 210 and the miniature spectrometer 100 may be disposed on a same surface of the base 280, or on different surfaces of the base 280.

For example, the base 280 may be formed of a light-transmissive material, and the light source 210 and the miniature spectrometer 100 may be disposed on one surface of the base 280 and spaced apart from each other. In particular, the light source 210 may be disposed so as to irradiate excited light LE upon the object OBJ after propagating through the base 280, and the miniature spectrometer 100 may be disposed so as to sense scattered light LS received from the object OBJ, which is incident after propagating through the base 280.

In this case, on an opposite surface of the base 280, an optical lens 260 configured for focusing the excited light LE from the light source 210 on the object OBJ and focusing the scattered light LS from the object OBJ on the miniature spectrometer 100 may be further included.

The base 280 may be formed of a flexible material. In this case, the miniature spectrometer module 1000 may be implemented so as to be wearable on the object OBJ, such as, for example, being implemented in a suitable shape which is designed to be wearable on the object OBJ. For example, the miniature spectrometer module 1000 may be implemented as a wrist-oriented noninvasive blood sugar sensor.

According to the present exemplary embodiment, the control unit 600 may be connected to the miniature spectrometer 100 in a wired or wireless manner. The control unit 600 may be mounted on the base 280 together with the miniature spectrometer 100, thereby forming, for example, a bracelet-shaped wearable miniature spectrometer.

Alternatively, the miniature spectrometer module 1000 may be implemented such that only the light source 210, the miniature spectrometer 100, and the like are formed as a bracelet-shaped wearable device, and the control unit 600 is included in a mobile device.

As described above, according to the one or more of the above-described exemplary embodiments, because the miniature spectrometer described above is miniaturized enough to be realizable as an on-chip, whereas a conventional spectrometer has a relatively large volume due to the use of a grating for scattering light by using a difference in a diffraction angle according to wavelengths of the light, the miniature spectrometer according to one or more exemplary embodiments may be included in a wrist-oriented noninvasive sensor and the like.

Although a miniature spectrometer and a miniature spectrometer module employing the same, according to the exemplary embodiments, have been described with respect to the accompanying drawings, these are only illustrative, the exemplary embodiments are not limited thereto, and various modifications and other embodiments may be formed.

It should be understood that the exemplary embodiments described therein should be considered in a descriptive sense only and not for purposes of limitation. Descriptions of features or aspects within each exemplary embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:

1. A spectrometer comprising:
a band-pass filter which is configured to transmit input light in a surface plasmon mode and which comprises:
a base layer formed of a first dielectric material,
a plurality of metal stripes disposed on the base layer, and
an array of cover layers configured to respectively cover the plurality of metal stripes with a second dielectric material that is different from the first dielectric material;
an in-coupler configured to couple the transmitted input light to a first end of the band-pass filter; and
an array of optical detectors configured to detect respective lights which are output from a second end of the band-pass filter.

2. The spectrometer of claim 1, wherein each respective cover layer included in the array of cover layers is formed with a different respective refractive index which corresponds to a respective transmission wavelength band.

3. The spectrometer of claim 2, wherein the cover layers included in the array of cover layers are spaced apart from each other.

4. The spectrometer of claim 1, wherein each of the plurality of metal stripes is formed such that at least a portion thereof protrudes from the base layer.

5. The spectrometer of claim 1, wherein each of the plurality of metal stripes has a respective width which is less than or equal to about 10 μm.

6. The spectrometer of claim 5, wherein each of the plurality of metal stripes has a respective thickness which is less than or equal to about 100 nm.

7. The spectrometer of claim 1, wherein the in-coupler is disposed so as to direct the input light to at least one of a boundary surface between a respective metal stripe and a respective cover layer and a boundary surface between a respective metal stripe and the base layer for each of the array of waveguides.

8. The miniature spectrometer of claim 1, wherein the in-coupler includes a grating in-coupler.

9. The spectrometer of claim 8, wherein the grating in-coupler has a period which is less than or equal to about 10 μm.

10. The spectrometer of claim 1, wherein the array of optical detectors are integrated with the second end of the array of waveguides.

11. A spectrometer module comprising:
a light source configured to emit excited light upon an object;
a band-pass filter which is configured to transmit input light in a surface plasmon mode and which comprises:
a base layer formed of a first dielectric material,
a plurality of metal stripes disposed on the base layer, and
an array of cover layers configured to respectively cover the plurality of metal stripes with a second dielectric material that is different from the first dielectric material;
an in-coupler configured to couple the transmitted input light to a first end of the band-pass filter; and
an array of optical detectors configured to detect respective lights which are output from a second end of the band-pass filter,
wherein the spectrometer is configured to sense a scattered light which is generated due to the emission of the excited light upon the object.

12. The spectrometer module of claim 11, further comprising a base,
wherein the light source is disposed on a first surface of the base, and the spectrometer module is disposed on any one of the first surface of the base and a second surface of the base which is different from the first surface.

13. The spectrometer module of claim 12, wherein the base is formed of a flexible material.

14. The spectrometer module of claim 11, wherein the spectrometer module is configured to be wearable on the object.

15. The miniature spectrometer module of claim 11, wherein the spectrometer is configured to sense at least one of scattered light which is reflected from the object and scattered light which has propagated through the object.

16. The spectrometer module of claim 11, further comprising a signal processor configured to analyze at least one physical property of the object based on a signal sensed by the spectrometer.

17. The spectrometer module of claim 16, further comprising a display device configured to display a result based on the analyzing by the signal processor.

18. The spectrometer module of claim 11, wherein the spectrometer module is configured to analyze at least one physical property of the object based on at least one of a near-infrared (NIR) absorption spectral analysis method which includes irradiating light of an NIR band from the light source and a laser Raman spectroscopy method which includes irradiating a laser beam from the light source.

19. A spectrometer comprising:
a band-pass filter which is configured to transmit an input light in a surface plasmon mode and includes:
a base layer formed of a first dielectric material,
a plurality of metal stripes buried in the base layer, and
an array of cover layers that are respectively disposed on the plurality of metal stripes with a second dielectric material that is different from the first dielectric material;
an in-coupler configured to couple the transmitted input light to a first end of the band-pass filter; and
an array of optical detectors configured to detect respective lights which are output from a second end of the band-pass filter.

\* \* \* \* \*